US012337137B1

(12) United States Patent
Abal et al.

(10) Patent No.: US 12,337,137 B1
(45) Date of Patent: Jun. 24, 2025

(54) PATIENT SIMULATOR

(71) Applicant: CareFusion 303, Inc., San Diego, CA (US)

(72) Inventors: Daniel M. Abal, San Diego, CA (US); Brendan John Burgess, Jr., Poway, CA (US); Brandon Fridley, San Diego, CA (US)

(73) Assignee: CAREFUSION 303, INC., San Diego, CA (US)

( * ) Notice: Subject to any disclaimer, the term of this patent is extended or adjusted under 35 U.S.C. 154(b) by 0 days.

(21) Appl. No.: 18/617,065

(22) Filed: Mar. 26, 2024

(51) Int. Cl.
*A61M 5/142* (2006.01)
*G16H 50/50* (2018.01)
*G16H 50/70* (2018.01)

(52) U.S. Cl.
CPC ............ *A61M 5/142* (2013.01); *G16H 50/50* (2018.01); *G16H 50/70* (2018.01); *A61M 2005/14208* (2013.01); *A61M 2005/14292* (2013.01); *A61M 2205/50* (2013.01)

(58) Field of Classification Search
CPC ........ A61M 5/142; A61M 2005/14208; A61M 2005/14292; G16H 50/50; G16H 50/70
USPC ....................................................... 604/151
See application file for complete search history.

(56) References Cited

U.S. PATENT DOCUMENTS

| 2002/0040208 A1 | 4/2002 | Flaherty et al. |
| 2021/0361863 A1 | 11/2021 | Burgess et al. |
| 2022/0199217 A1* | 6/2022 | Park ................... G16B 40/00 |

FOREIGN PATENT DOCUMENTS

| CN | 205144524 U | 4/2016 |
| WO | WO-2023122514 A1 | 6/2023 |

OTHER PUBLICATIONS

International Search Report and Written Opinion for Application No. PCT/US2023/026773, dated Feb. 29, 2024, 22 pages.
Invitation to Pay Additional Fees and Partial International Search Report for Application No. PCT/US2023/026773. dated Jan. 8, 2024, 13 pages.
1 Extended European Search Report for Application No. 24219305.5, dated May 7, 2025, 12 pages.

* cited by examiner

*Primary Examiner* — Phillip A Gray
(74) *Attorney, Agent, or Firm* — Morgan, Lewis & Bockius LLP

(57) ABSTRACT

An infusion control test system includes a patient bio-simulator configured to generate first simulated biophysical data; an infusion control system configured to determine a first infusion profile in response to the first simulated biophysical data; and an infusion pump simulator configured to simulate a first administration of medication according to the first infusion profile. The patient bio-simulator is further configured to: simulate a patient response to the simulated first administration of medication; and generate second simulated biophysical data by adjusting the first simulated biophysical data according to the patient response.

20 Claims, 6 Drawing Sheets

400 ↘

---

Blood Pressure 402
    Application to simulate:
        Vasopressor CL and pause
    Conditions to simulate:
        Normal BP
        Abnormal BP: low, high

---

Blood Glucose 404
    Application to simulate:
        Insulin IV infusion CL and pause
    Conditions to simulate:
        Normal glycemic level: 70-100
        Abnormal conditions: hypoglycemic <70, hyperglycemic > 150

---

Breathing 406           (capnography)
    Application to simulate:
        PCA pause
    Conditions to simulate:
        Normal breathing rate and mmHg etCO2
        Abnormal conditions: hypoventilation, hyperventilation, hypocapnia,
                  hypercarbia, rebreathing, apnea

---

Pulse Oximetry 408      (capnography)
    Application to simulate:
        PCA pause
    Conditions to simulate:
        Normal SPO2: 95-100%
        Abnormal SPO2: <95%

FIG. 4

PATIENT SIMULATOR

TECHNICAL FIELD

The present disclosure relates, generally, to infusion device testing systems and, more particularly, to the use of patient response simulations in the testing of infusion devices.

BACKGROUND

Infusion pumps are complex electromechanical devices used to deliver fluids into a patient's body in a controlled manner. They typically serve the needs of hospital-bound patients, where life-saving medication is normally delivered via intravenous infusion. Infusion pump systems typically comprise a plurality of modules configured for different programming and pumping functions. These modules normally work together, using compatible power specifications, communication protocols, and mechanical interconnects.

Due to the complexity of infusion pumps, as well as the important role they play in patient treatment, it is essential to subject infusion pump designs to rigorous testing. Traditional infusion pump testing systems require a patient to be connected to biosensors to measure the system response to titration of medication with an infusion pump system. For example, a patient must be connected to a continuous blood glucose sensor to simulate blood glucose. To simulate depth of anesthesia, a patient must be connected to a BIS sensor to generate the various EMG signals. When a patient is not used, complicated simulation devices are required to simulate patient physiological signals. For example, a sophisticated valving system and CO2 tanks are required to simulate breathing and etCO2 measurements. To simulate blood pressure, a source of pressure and a controller are required to simulate a patient's arterial pressure on a pressure bio-sensor.

Unfortunately, testing systems that require a patient to be connected to biosensors are inconvenient and yield patient-specific results. In addition, complex mechanical testing jigs require regular maintenance and can be difficult to configure.

SUMMARY

The present disclosure provides devices, systems, and methods that address some of the aforenoted problems and other problems associated with diagnostic testing and infusion devices. Much of the present disclosure is directed to a patient simulator that generates physiological patient data (simulating patient vital signs) in the form of signals that are used as inputs to the infusion control system in a testing environment. The simulator generates these signals using algorithms to model patient response, and uses machine learning with existing clinical files to generate the response to various medications, operations, and situations based on multiple patient clinical databases and a cohort of patient models. Example implementations of the advancements discussed herein include the following:

In one aspect, an infusion control test system includes a patient bio-simulator configured to generate first simulated biophysical data; an infusion control system configured to determine a first infusion profile in response to the first simulated biophysical data; and an infusion pump simulator configured to simulate a first administration of medication according to the first infusion profile. The patient bio-simulator is further configured to simulate a patient response to the simulated first administration of medication, and generate second simulated biophysical data by adjusting the first simulated biophysical data according to the patient response.

In some implementations, the infusion control system is further configured to determine a second infusion profile in response to the second simulated biophysical data; the infusion pump simulator is further configured to simulate a second administration of medication according to the second infusion profile; and the patient bio-simulator is further configured to simulate an updated patient response to the simulated second administration of medication, and generate third simulated biophysical data by adjusting the second simulated biophysical data according to the updated patient response.

In some implementations, the patient bio-simulator is configured to generate the first simulated biophysical data by using one or more algorithms that model patient vital signs. In some implementations, the one or more algorithms use machine learning with existing clinical files to model patient vital signs in response to one or more medications, operations, or scenarios based on multiple patient clinical databases and a cohort of patient models.

In some implementations, the first simulated biophysical data includes a blood pressure level, a blood glucose level, a breathing rate, or an oxygen saturation rate. In some implementations, the second simulated biophysical data includes an adjusted blood pressure level, an adjusted blood glucose level, an adjusted breathing rate, or an adjusted oxygen saturation rate.

In some implementations, the first infusion profile specifies an infusion rate and an infusion amount for a particular medication. In some implementations, the infusion pump simulator is configured to simulate the first administration of medication by simulating output of the particular medication in accordance with the infusion rate and the infusion amount.

In some implementations, the first infusion profile specifies an infusion rate for a particular medication, and the infusion pump simulator is configured to simulate the first administration of medication according to an accelerated simulation rate that is higher than the infusion rate. In some implementations, the patient bio-simulator is configured to simulate the patient response according to the accelerated simulation rate.

In another aspect, a computer-implemented method for operating an infusion control test system includes causing a computer-implemented patient bio-simulator to generate first simulated biophysical data, causing an infusion control system to determine a first infusion profile in response to the first simulated biophysical data, and causing an infusion pump simulator to simulate a first administration of medication according to the first infusion profile. The method further includes causing the patient bio-simulator to simulate a patient response to the simulated first administration of medication, and generate second simulated biophysical data by adjusting the first simulated biophysical data according to the patient response.

In some implementations, the method further includes causing the infusion control system to determine a second infusion profile in response to the second simulated biophysical data; causing the infusion pump simulator to simulate a second administration of medication according to the second infusion profile; and causing the patient bio-simulator to simulate an updated patient response to the simulated second administration of medication, and generate third simulated biophysical data by adjusting the second simulated biophysical data according to the updated patient response.

In some implementations, the patient bio-simulator generates the first simulated biophysical data by using one or more algorithms that model patient vital signs. In some implementations, the one or more algorithms use machine learning with existing clinical files to model patient vital signs in response to one or more medications, operations, or scenarios based on multiple patient clinical databases and a cohort of patient models.

In some implementations, the first simulated biophysical data includes a blood pressure level, a blood glucose level, a breathing rate, or an oxygen saturation rate. In some implementations, the second simulated biophysical data includes an adjusted blood pressure level, an adjusted blood glucose level, an adjusted breathing rate, or an adjusted oxygen saturation rate.

In some implementations, the first infusion profile specifies an infusion rate and an infusion amount for a particular medication. In some implementations, the infusion pump simulator simulates the first administration of medication by simulating output of the particular medication in accordance with the infusion rate and the infusion amount.

In some implementations, the first infusion profile specifies an infusion rate for a particular medication, and the infusion pump simulator simulates the first administration of medication according to an accelerated simulation rate that is higher than the infusion rate. In some implementations, the patient bio-simulator simulates the patient response according to the accelerated simulation rate.

Although the present disclosure describes the subject technology in the context of syringe pumps, much of the subject technology is nonetheless applicable to other types of infusion pumps. It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

For a better understanding of the various described implementations, reference should be made to the Detailed Description, below, in conjunction with the following drawings. Like reference numerals refer to corresponding parts throughout the figures and description.

FIG. 4 depicts examples of patient simulation modules, according to various aspects of the subject technology.

DETAILED DESCRIPTION

Reference will now be made to implementations, examples of which are illustrated in the accompanying drawings. In the following description, numerous specific details are set forth in order to provide an understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

The following figures illustrate exemplary devices, systems, and methods, which can be used to improve infusion pump testing systems. As discussed in more detail herein, a patient simulator generates physiological patient data (simulating patient vital signs) in the form of signals that are used as inputs to the infusion control system in a testing environment. The simulator generates these signals using algorithms to model patient response, and uses machine learning with existing clinical files to generate the response to various medications, operations and situations based on multiple patient clinical databases and cohort of patient models.

To provide a better understanding of the various components of an infusion pump testing system, the following discussion (with reference to FIGS. 1A, 1B, and 2) describes example components and operations of an infusion pump system.

Figure 1A:
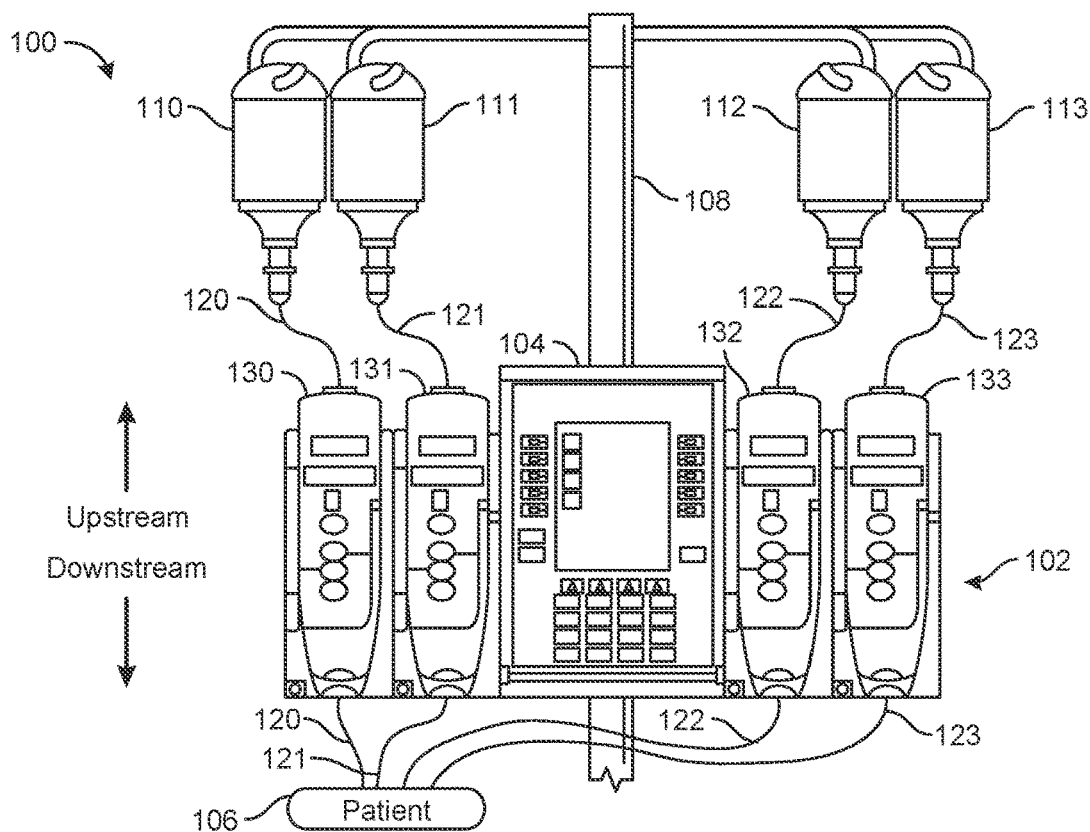
FIGS. 1A and 1B depict an example patient care system that includes infusion pumps mounted to a control unit, according to various aspects of the subject technology.
Figure 1B:
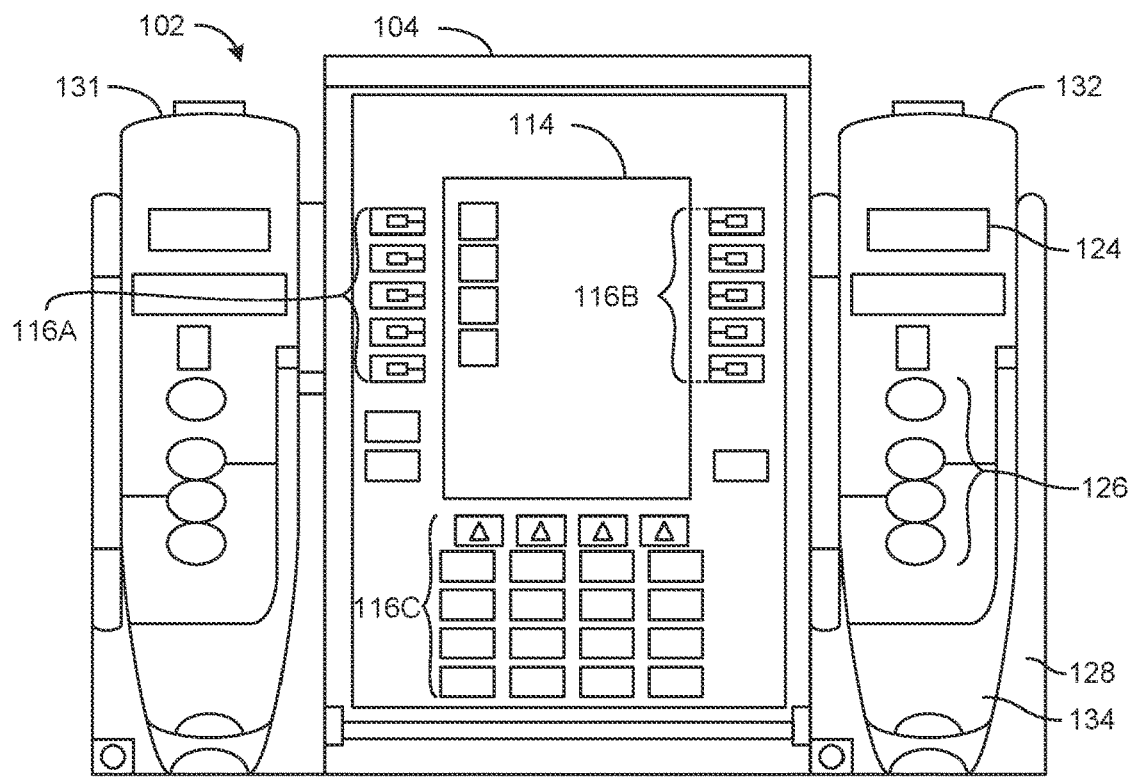

FIGS. 1A and 1B depict an example patient care system that includes infusion pumps mounted to a control unit, according to various aspects of the subject technology. The patient care system 100 shown in FIG. 1A includes four infusion pumps 130-133, each of which is in operative engagement with a respective administration set 120-123 (e.g., silicon tubing). The administration sets 120-123 connect the infusion pumps 130-133 to fluid supplies 110-113, which are inverted and suspended above the infusion pumps 130-133. The fluid supplies 110-113 are depicted as bottles in FIG. 1A, but they may take other forms (e.g., bags). Both the fluid supplies 110-113 and the patient care device 102 are mounted to a roller stand 108.

The fluid supplies 110-113, as well as their orientation (e.g., mount location, mount height, mount type) within the care area, may generate one or more interaction records. The interaction record for a set, for example, may be generated in part by detecting a scannable code associated with the set or by detecting a physical structure on the set that encodes identifying information for the set prior to use.

As shown in FIG. 1A, each administration set 120-123 is connected between a respective fluid supply 110-113 and a patient 106 so that the patient 106 may receive the fluids in any or all of the fluid supplies 110-113. Each of the administration sets 120-123 may be identified either actively (e.g., by clinician scanning) or passively (e.g., by wireless or optical detection). Typically, medical administration sets have more parts than are shown in FIG. 1A. Many have check valves, drip chambers, valved ports, connectors, and other devices well known to those skilled in the art. These other devices are not included in the drawings to preserve clarity of illustration. These other devices In the depicted example, a separate infusion pump 130-133 is used to infuse each of the respective fluids of the fluid supplies 110-113 into the patient 106. The infusion pumps 130-133 are flow control devices that act on the respective tube or fluid conduit of the respective administration set 120-123 to move fluid from the fluid supply 110-113, through the conduit, and to the patient. Because individual infusion pumps 130-133 are used, each of the infusion pumps 130-133 may be individually set to the pumping or operating parameters required for infusing the particular medical fluid from the respective fluid supply 110-113 into the patient at the particular rate prescribed for that fluid by the clinician.

FIG. 1B depicts a portion of the patient care device 102 shown in FIG. 1A. The illustrated patient care device 102 includes a control unit 104, along with two of the infusion pumps 131 and 132 mounted at either side of the control unit 104. In some implementations, the control unit 104 is configured for programming each of the infusion pumps 130-133 (see FIG. 1A). FIG. 1B also shows the displays and controls of the infusion pumps 131 and 132, such as the display 124 and the controls 126 of the infusion pump 132.

Each of the infusion pumps 130-133 may include a door and a handle. For example, infusion pump 132 includes door 128 and handle 134. The handle 134 operates to lock the door 128 in a closed position during operation. The handle 134 also operates to unlock and open the door for loading an administration set (e.g., administration set 122) and for accessing the internal pumping and sensing mechanisms of the infusion pump 132. While the door 128 is open, the administration set 122 can be connected with the infusion pump 132. While the door 128 is closed, the administration set 122 is brought into operative engagement with a pumping mechanism, upstream and downstream pressure sensors, and/or other equipment of the infusion pump 132.

Each of the infusion pumps 130-133 may also include a display. For example, in the depicted implementation, the display 124 of the infusion pump 132 (e.g., an LED display) is located in plain view on the door 128 and may be used to visually communicate information regarding the infusion pump 132. For example, the display 124 can communicate alert indications (e.g., alarm messages). Additionally, the control keys 126 allow for programming and controlling operations of the infusion pump as desired. In some implementations, the control keys may be presented as interactive elements on the display 124 (e.g., a touchscreen display). The patient care device 102 and/or infusion pump 132 may also include audio alert equipment in the form of a speaker.

The control unit 104 of the patient care device 102 also includes a display 114 for visually communicating various information, such as the operating parameters of a connected pump or alert indications and alert messages. The control unit 104 also includes control keys 116A-C for selecting or setting control parameters and/or options for controlling the control unit 104 and modules connected thereto (e.g., infusion pumps 130-133).

In addition to the display 114 and the control keys 116A-C, the control unit 104 may also include a speaker to provide audible alerts. In some implementations, the display 114 is implemented as a touchscreen display. In such implementations, the control keys 116A-C may be omitted or reduced in number by providing corresponding interactive elements via a graphical user interface presented via the display 114. In some implementations, the control keys 116A-C may select a corresponding option displayed in display 114.

The control unit 104 may also include a communications system by which the control unit 104 can communicate with external equipment, such as a medical facility server, a handheld communication device, a laptop-type computer, or other information device that a clinician may have to transfer information or to download drug libraries to the control unit 104.

The communication module may be used to transfer access or interaction information for clinicians encountering the control unit 104 or a device coupled thereto (e.g., infusion pumps 130-133, or bar code scanner). The communications system may include one or more of a radio frequency (RF) system, an optical system such as infrared, a BLUETOOTH™ system, or other wired or wireless system. The bar code scanner and communications system may alternatively be included integrally with the infusion pumps 130-133, such as in cases where a control unit is not used, or in addition to one with the control unit 104. Further, information input devices need not be hard-wired to medical instruments, information may be transferred through a wireless connection as well. Additionally, other types of modules may be connected to the infusion pumps 130-133 or to the control unit 104 such as a syringe pump module, a patient controlled analgesic module, an end-tidal CO2 monitoring module, an oximeter monitoring module, or the like.

Figure 2:
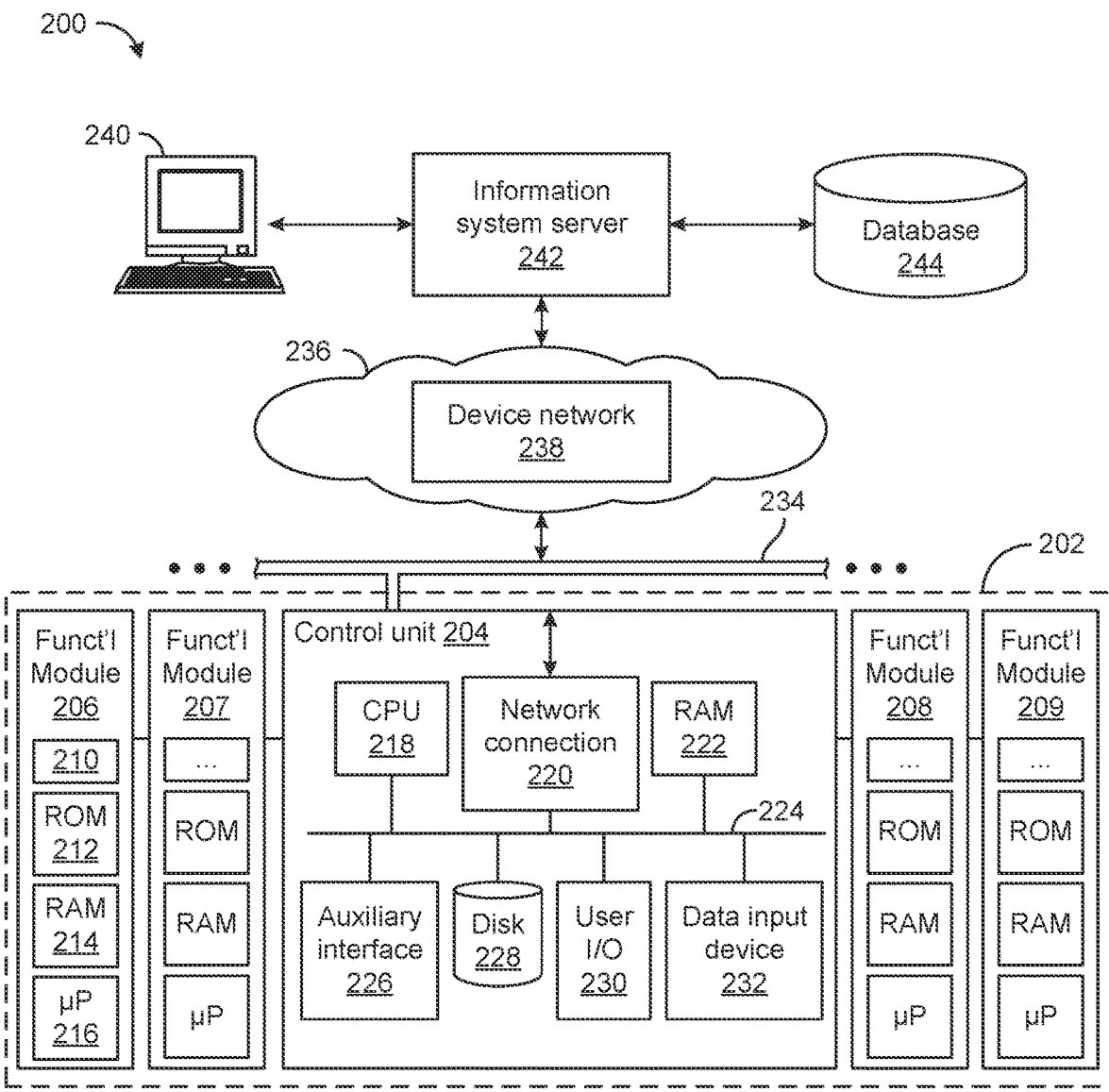
FIG. 2 depicts an example institutional patient care system of a healthcare organization, according to various aspects of the subject technology.

FIG. 2 depicts an example institutional patient care system 200 of a healthcare organization, according to various aspects of the subject technology. In FIG. 2, a patient care device 202 (e.g., patient care device 102 of FIGS. 1A and 1B) is connected to an internal healthcare network 236. The term patient care device ("PCD") may be used interchangeably with the term patient care unit ("PCU"), either of which may include various ancillary medical devices, such as an infusion pump (e.g., infusion pumps 130-133 of FIG. 1A), a vital signs monitor, a medication dispensing device (e.g., cabinet, tote), a medication preparation device, an automated dispensing device, a module coupled with one of the aforementioned (e.g., a syringe pump module coupled with an infusion pump), and the like. Each element of the patient care device 202 is connected to an internal healthcare network 236 by a transmission channel 234. The transmission channel 234 can be a wired or wireless transmission channel, such as an 802.11 wireless local area network (LAN).

In some implementations, the internal healthcare network 236 also includes computer systems located in various departments throughout a hospital or healthcare center. For example, the internal healthcare network 236 optionally includes computer systems associated with an admissions department, a billing department, a biomedical engineering department, a clinical laboratory, a central supply department, one or more unit station computers, and/or a medical decision support system. As described further below, the internal healthcare network 236 may include discrete sub-networks. In the depicted example, the internal healthcare network 236 includes a device network 238 by which the patient care device 202 and other devices can communicate in accordance with normal operations.

The institutional patient care system 200 may also incorporate a separate information system server 242 (e.g., a health information system server). Moreover, although the information system server 242 is shown as a separate server, the functions and programming of the information system server 242 may be incorporated into another computer. The institutional patient care system 200 may further include a device terminal 240 for connecting and communicating with the information system server 242. The device terminal 240 may include personal computers, personal data assistants, or mobile devices (e.g., laptops, tablet computers, augmented reality devices, or smartphones) configured with software for communications with information system server 242 via the internal healthcare network 236.

Patient care device 202 comprises a system for providing patient care, and it may include or incorporate infusion pumps (e.g., infusion pumps 130-133 of FIG. 1A), physiological monitors (e.g., heart rate, blood pressure, ECG, EEG, pulse oximeter, and other monitors), therapy devices, and other drug delivery devices that may be utilized according to the teachings set forth herein.

In the depicted example, patient care device 202 comprises a control unit 204 (e.g., control unit 104 of FIGS. 1A and 1B), also referred to as interface unit 204, connected to one or more functional modules 206-209 (e.g., infusion pumps 130-133 of FIG. 1A). Control unit 204 includes a central processing unit (CPU) 218 connected to a memory, for example, random access memory (RAM) 222, and one or more interface devices such as user interface device 230, a coded data input device 232, a network connection 220, and an auxiliary interface 226 for communicating with additional modules or devices. Control unit 204 also, although not necessarily, includes a main non-volatile storage unit 228, such as a hard disk drive or non-volatile flash memory, for storing software data. Additionally, control unit 204 may include one or more internal buses 224 for interconnecting the aforementioned elements.

In various implementations, user interface device 230 is a touch screen for displaying information to a user and allowing a user to input information by touching defined areas of the screen. Additionally, or in the alternative, user interface device 230 could include any means for displaying and inputting information, such as a monitor, a printer, a keyboard, softkeys, a mouse, a track ball, and/or a light pen.

Data input device 232 may be a bar code reader capable of scanning and interpreting data printed in bar coded format. Additionally, or in the alternative, data input device 232 can be any device for entering coded data into a computer, such as a device(s) for reading magnetic strips, radio-frequency identification (RFID) devices whereby digital data encoded in RFID tags or smart labels (defined below) are captured by the data input device 232 via radio waves, PCMCIA smart cards, radio frequency cards, memory sticks, CDs, DVDs, or any other analog or digital storage media. Other examples of the data input device 232 include a voice activation or recognition device or a portable personal data assistant (PDA). Depending upon the types of interface devices used, the user interface device 230 and the data input device 232 may be the same device. Although the data input device 232 is shown in FIG. 2 as being disposed within the control unit 204, the data input device 232 may be external to the control unit 204 (e.g., at the device terminal 240).

Auxiliary interface 226 may be an RS-232 communications interface, however any other means for communicating with a peripheral device (e.g., a printer, a patient monitor, an infusion pump, or another medical device) may be used without departing from the subject technology. Additionally, the data input device 232 may be a separate functional module (e.g., functional modules 206-207) configured to communicate with the control unit 204 or any other system on the network using suitable programming and communication protocols.

Network connection 220 may be a wired or wireless connection, such as by Ethernet, Wi-Fi, BLUETOOTH, an integrated services digital network (ISDN) connection, a digital subscriber line (DSL) modem or a cable modem. Any direct or indirect network connection may be used, including, but not limited to a telephone modem, an MIB system, an RS232 interface, an auxiliary interface, an optical link, an infrared link, a radio frequency link, a microwave link or a WLANS connection or other wireless connection.

The functional modules 206-209 are devices (e.g., infusion pumps 130-133 of FIG. 1A) for providing care to a patient or for monitoring patient conditions. As shown in FIG. 2, at least one of functional modules 206-209 may be an infusion pump module such as an intravenous infusion pump for delivering medication or other fluid to a patient. For the purposes of this discussion, functional module 206 is an infusion pump module. Each of functional modules 206-209 may be any patient treatment or monitoring device including, but not limited to, an infusion pump, a syringe pump, a PCA pump, an epidural pump, an enteral pump, a blood pressure monitor, a pulse oximeter, an EKG monitor, an EEG monitor, a heart rate monitor, an intracranial pressure monitor, or the like. Additionally, the functional modules 206-209 may include a printer, a scanner, a bar code reader, a near-field communication reader, an RFID reader, or any other peripheral input, output or input/output device.

Each functional module 206-209 communicates directly or indirectly with control unit 204, providing overall monitoring and control of the patient care device 202. Additionally, the functional modules 206-209 may be connected physically and electronically in serial fashion to one or both ends of control unit 204 as shown in FIG. 2. However, it is recognized that there are other means for connecting the functional modules 206-209 with the control unit 204 that may be utilized without departing from the subject technology. It is also appreciated that devices such as pumps or patient monitoring devices that provide sufficient programmability and connectivity may be capable of operating as stand-alone devices and may communicate directly with the internal healthcare network 236 without being connected through the control unit 204 or a separate interface unit. As described above, additional medical devices or peripheral devices may be connected to the patient care device 202 through one or more auxiliary interfaces 226.

Each of the functional modules 206-209 may include a microprocessor 216, a volatile memory 214, a nonvolatile memory 212, and module-specific components 210. It should be noted that while four functional modules are shown in FIG. 2, any number of devices may be connected directly or indirectly to the control unit 204. The number and type of functional modules described herein are intended to be illustrative, and they in no way limit the scope of the subject technology. The module-specific components 210 include any components necessary for operation of a particular module, such as a pumping mechanism for the functional module 206.

While each of the functional modules 206-209 may be capable of a least some level of independent operation, the control unit 204 monitors and controls overall operation of the patient care device 202. For example, as will be described in more detail below, the control unit 204 provides programming instructions to the functional modules 206-209 and monitors the status of each of the functional modules 206-209.

Medical devices incorporating aspects of the subject technology may be equipped with a network interface module (NIM), allowing the medical device to participate as a node in a network. While for purposes of clarity the subject technology will be described as operating in an Ethernet network environment using the Internet Protocol (IP), it is understood that concepts of the subject technology are equally applicable in other network environments, and such environments are intended to be within the scope of the subject technology.

Data to and from the various data sources can be converted into network-compatible data with existing technology, and movement of the information between the medical device and network can be accomplished by a variety of means. For example, the patient care device 202 and the internal healthcare network 236 may communicate via automated interaction, manual interaction, or a combination of both automated and manual interaction. Automated interaction may be continuous or intermittent and may occur through the network connection 220, as shown in FIG. 2, or through RS232 links, MIB systems, RF links such as BLUETOOTH, IR links, WLANS, digital cable systems, telephone modems, or other wired or wireless communication means.

Manual interaction between the patient care device 202 and the internal healthcare network 236 involves physically transferring, intermittently or periodically, data between systems using, for example, the user interface device 230, the coded data input device 232, bar codes, computer disks, portable data assistants, memory cards, or any other media for storing data. The communication means in various aspects is bidirectional with access to data from as many points of the distributed data sources as possible. Decision-making can occur at a variety of places within the internal healthcare network 236. For example, and not by way of limitation, decisions can be made in the information system server 242, decision support, a remote data server, hospital department or unit stations, or within the patient care device 202 itself.

According to various implementations, the information system server 242 includes a formulary and/or pharmacy information system. Pharmacy information systems may enable a safer physician medication order process. A pharmacy website (e.g., provided by the information system server 242) may provide the physician with a list of available drugs from which the physician may select. The pharmacy website may contain a drug library having the list of available drugs but may also contain and present to the physician the drug names associated with recommended dosages and dose limits that have been established or adopted by the healthcare facility. In such a case where the physician need only select items from the computer screen rather than having to manually type in drug names and drug administration numbers (such as infusion rates, times, etc.) associated with administration of the medication, a more accurate medication process should result.

If a clinical order is for administration of a particular medication regimen, the order will be transmitted to the pharmacy's system server (e.g., information system server 242). The pharmacy reviews the order, and once the order has been prepared, the order may be transmitted to the nurse station for matching with the appropriate patient. Within a formulary, there may be indication for use information and/or concentrations and drug ranges approved for the facility. A formulary is an approved list of drugs for use (e.g., available to order for a patient) within a medical facility. As will be described further, a formulary may be used to define one or more medical device drug libraries, which may then be provided to infusion pumps within a hospital network (e.g., internal healthcare network 236).

Inside the drug library, there is medication information such as drug names, concentration, diluent volume, strength, minimum or maximum infusion parameters for a drug, and other parameters. The establishment of these parameters, along with parameters for off-formulary orders, via the information pharmacy's system server is useful for maintaining consistency across the healthcare environment and ensuring an order is intelligible and executed according to expectations by other devices (e.g., patient care device 202) within the pharmacy's system server.

With further reference to FIG. 2, the patient care device 202 is capable of operating in several different modes, or personalities, with each personality defined by a configuration database. The configuration database may be a database internal to the patient care device 202, or an external database 244. A particular configuration database is selected based, at least in part, by patient-specific information such as patient location, age, physical characteristics, or medical characteristics.

Medical characteristics include, but are not limited to, patient diagnosis, treatment prescription, medical history, medical records, patient care provider identification, physiological characteristics or psychological characteristics. As used herein, patient-specific information also includes care provider information (e.g., physician identification) or the location of the patient care device 202 location in the hospital or hospital computer network. Patient care information may be entered through any of the network connection 220, the user interface device 230, the data input device 232, or the auxiliary interface 226. Additionally, patient care information may originate from anywhere in the internal healthcare network 236, such as from a pharmacy server, an admissions server, a laboratory, and the like.

The memory of the control unit 204 (e.g., RAM 222 or the main non-volatile storage unit 228) may contain a drug library, an event log, and/or infusion pump configuration settings, such as profiles to be used in particular practice areas (e.g., ICU, PED, etc.). The control unit 204 memory may be electronically loadable memory such as non-volatile memory (e.g., EEPROM). Drug libraries stored on pumps, which illustratively contain such information as the drug names, ranges of delivery parameter values such as proper concentrations, dosage units, and dose limits, can be used to perform drug-calculation-based infusions in a clinical setting.

A drug library stored within the pump's memory may include clinical order settings such as limits set by the clinical institution for each drug of the library (also termed as "guardrails" herein). Such limits may take the form of maximum and minimum dosages for each drug which may be made dependent on patient factors or other factors associated with delivery of the drug. For example, the dosage limits may vary depending on the weight of the patient or body surface area ("BSA"), depending on the unit or ward of the medical institution in which the drug is being used (for example neonatal care unit (NCU), the intensive care unit (ICU), etc.), and/or other factors. The limits may also include maximum and minimum flow rates, infusion times, or other infusion parameters for a given drug. As with the dosage limits, these limits may also vary depending on the weight or other physiological parameters of the patient. In some implementations, the drug library and/or guardrails are stored elsewhere, such as on the device terminal 240, the external database 244, or another device connected to the internal healthcare network 236.

An alarm may be provided if the nurse sets the pump to operate outside the range between the limits for a particular drug. In some cases, the alarm may be overridden and in other cases it may not. The medical facility may establish "soft" limits for each drug, which may be overridden by the nurse, and "hard" limits which may not. In either case where a limit is exceeded, a pump data log or other processor in communication with the infusion pump may record each such limit event for later analysis where the attempted setting is higher than the maximum or lower than the minimum dosage.

The pump may also include a display (e.g., display 114 of FIG. 1B) for displaying a user interface, which may include a control panel through which the user can program the programmable controller and a display screen for displaying drug entries from the drug library. Each of the associated sets of drug delivery parameters includes information selected from a group of parameters including drug concentration, drug delivery rate, drug dose, and bolus size. The electronically loaded drug library contains a list of available mode options specifying the units available for expressing drug delivery information, and the drug infusion pump offers the user the list of available mode options from which to make a selection when the electronically loaded drug library is in the pump.

In the case of a syringe pump, the electronically loaded drug library may include a list of names of syringe manufacturers identifying syringes that can be used in the drug infusion pump, and the drug infusion pump offers the user the list of names of syringe manufacturers from which to make a selection when the electronically loaded drug library is in the pump. The loaded drug library may include a list of syringe sizes identifying syringes that can be used in the drug infusion pump, and the drug infusion pump offers the user the list of syringe sizes from which to make a selection when the electronically loaded drug library is in said pump. In the case of a peristaltic pump, the electronically loaded drug library may include a list of infusion set manufacturers. A loaded drug library may include a set of features, each of which is either be toggled on or off, and the pump offers the user only the features from among the set of features that are toggled on when the electronically loaded drug library is in said pump.

Figure 3:
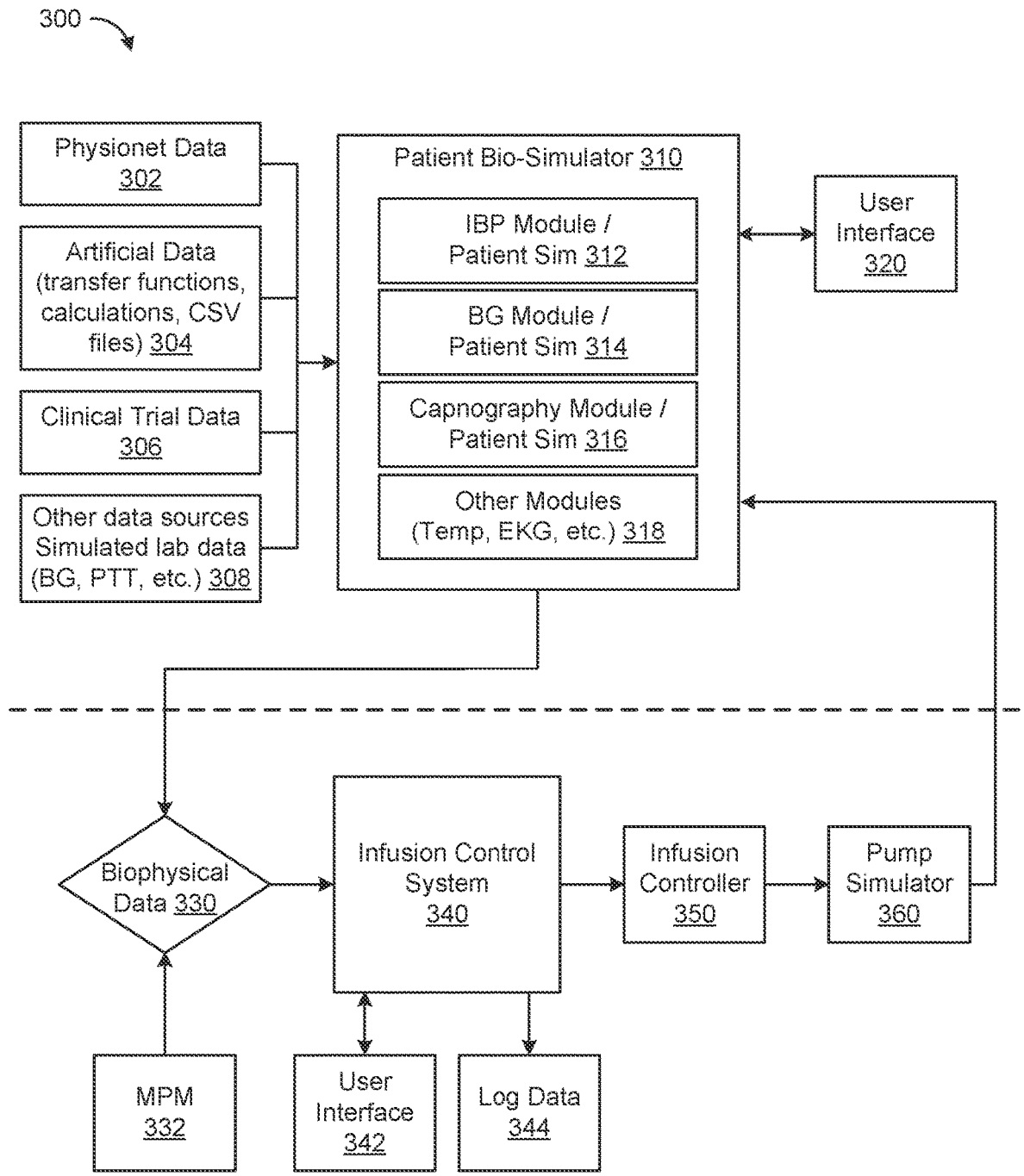
FIG. 3 depicts an infusion pump testing system, according to various aspects of the subject technology.

FIG. 3 depicts an infusion pump testing system 300, according to various aspects of the subject technology. System 300 includes a patient bio-simulator 310, which simulates biophysical data 330, also referred to as physiological patient data (vital signs) that is used as inputs to an infusion control system 340, also included in system 300. The infusion control system 340 generates infusion profiles that cause an infusion controller 350 to operate a pump simulator 360 to simulate the administration of medication to a patient. The simulated administration of medication causes the simulator 310 to simulate a patient response, and that response causes the simulated biophysical data to be adjusted.

The simulator 310 includes one or more patient simulation modules, including, for example, an invasive blood pressure (IBP) module 312 configured to generate simulated IBP signals, a blood glucose (BG) module 314 configured to generate simulated BG signals, a capnography module 316 configured to generate simulated capnography signals, and other modules 318 configured to generated simulated temperature, electrocardiogram (EKG), and other signals depending on the application.

FIG. 4 depicts examples of patient simulation modules 400, according to various aspects of the subject technology. The patient simulation modules 400 may be used by simulator 310 (FIG. 3) and are example modules provided for illustrative purposes. Blood pressure module 402 (e.g., corresponding to module 312, FIG. 3) simulates vasopressor CL and pause, and simulates normal blood pressure conditions and abnormal blood pressure conditions (high and low). Blood glucose module 404 (e.g., corresponding to module 314, FIG. 3) simulates insulin IV infusion CL and pause, by simulating blood pressure conditions such as normal glycemic levels (70-100) and abnormal conditions (hypoglycemic <70 and hyperglycemic >150). Breathing module 406 (e.g., corresponding to capnography module 316, FIG. 3) simulates PCA pause, by simulating normal breathing conditions (normal rate and mmHg etCO2) and abnormal breathing conditions (hypoventilation, hyperventilation, hypocapnia, hypercarbia, rebreathing, apnea). Pulse oximetry module 408 (e.g., corresponding to capnography module 316, FIG. 3) simulates PCA pause, by simulating normal SPO2 conditions (95-100%) and abnormal SPO2 conditions (<95%).

Returning to FIG. 3, the patient simulation modules generate the corresponding simulated data using one or more input sources, including, for example, PhysioNet data 302 (or any other repository of medical research data), artificial data 304 (including mathematical manipulations of that data), clinical trial data 306, and other data sources 308 of simulated lab data (such as simulated blood glucose (BG) data, simulated partial thromboplastin time (PTT) data, and so forth).

In general, the simulator 310 generates simulated biophysical data 330 using algorithms provided by each of the simulation modules to model patient responses. In some implementations, the algorithms are the result of machine learning. Specifically, simulator 310 may use machine learning with existing clinical files (e.g., any of 302-308) to generate the response to various medications, operations, and situations based on multiple patient clinical databases and a cohort of patient models (e.g., any of 302-308). In some implementations, a user interface 320 is provided, enabling manual configuration of input variables and other functions.

The infusion control system 341 may be a device under test, such as control unit 104 (FIGS. 1A-1B) or control unit 204 (FIG. 2). In general, the infusion control system 340 may be any device having a processor configured to generate infusion pump instructions (referred to herein as infusion profiles) based on input biophysical data. The input data may be simulated (output from simulator 310) when in a testing environment, or real (e.g., output from a multiparameter monitor (MPM) 332) when in a clinical environment. In some implementations, the infusion control system 340 may include or be coupled to a user interface 342, enabling manual configuration of control variables and other functions. In some implementations, the infusion control system 340 may output log data 344 during operations in the clinical setting or in the test setting. The log data may include real-time infusion control data (e.g., infusion profiles and corresponding input biophysical data 330) for purposes of analysis.

The infusion controller 350 may be included in the infusion control system 340 or otherwise coupled to the infusion control system 340, and may consist of a processor configured to control the pumping operations of an infusion pump in the clinical setting, or a pump simulator 360 in a test setting. The infusion controller 350 converts infusion profile data (e.g., infusion rate, timing, and other variables associated with an infusion routine) to instructions that are understandable by the infusion pump or pump simulator 360.

The pump simulator 360 simulates the administration of medication to a patient. Specifically, as described above with reference to the pumping operations of a patient care device 102 with respect to a patient 106 (FIGS. 1A-1B), the pump simulator 360 simulates mechanical pumping of a drug through an administration set into the patient. In system 300, however, rather than a patient 106 receiving the medication, the simulator 310 receives signals representing the administration of the medication and adjusts the biophysical data output accordingly.

The infusion pump testing system 300 is a closed loop control system. The system simulates sensor feedback from a patient (in the form of simulated biophysical data 330) and simulates the administration of medication based on the simulated patient's vital signs (in the form of pump simulator 360 executing an infusion profile and outputting corresponding signals back to the simulator 310). When the simulator 310 receives the administration signals outputted from the pump simulator 360, the simulator 310 responds by showing how a patient would react to that medication. The results of this reaction are embodied in adjusted simulated biophysical data 330, and the closed loop process continues with additional processing by the infusion control system 340 and adjusted infusion profiles being fed to the infusion controller 350.

For implementations in which the simulator 310 uses machine learning for modeling the biophysical data 330, the inputs (e.g., 302-308) optimize the system. Specifically, the inputs may take into account pharmokinetic conditions (how the body interacts with administered substances for the entire duration of exposure), accounts for factors involved with different patients, and models those inputs. Thus, the inputs themselves are more realistic.

Figure 5:
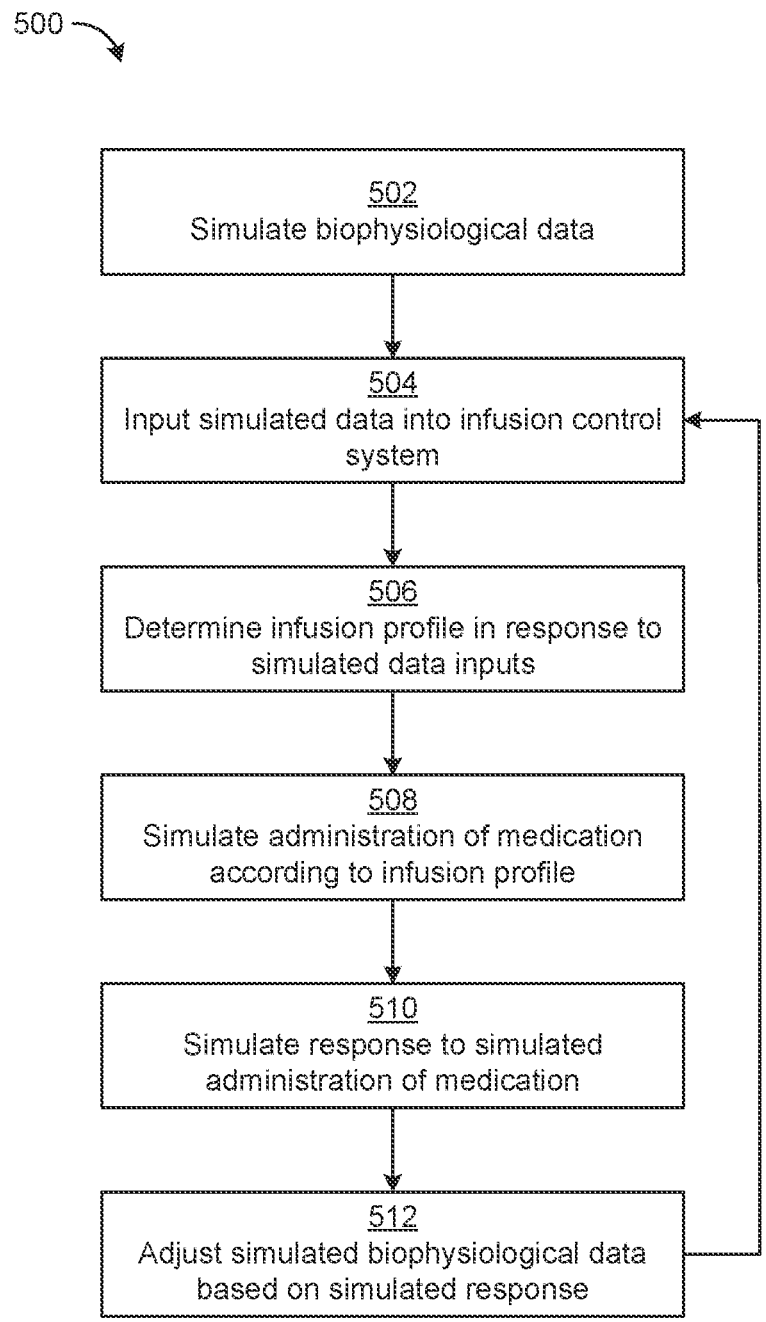
FIG. 5 depicts an example process for operating an infusion control test system, according to various aspects of the subject technology.

FIG. 5 depicts an example process 500 for operating an infusion control test system, according to various aspects of the subject technology. For explanatory purposes, the present disclosure describes the blocks of example process 500 with reference to FIGS. 1-4, including the components and/or processes described therein. One or more of the blocks of process 500 may be implemented by one or more of the computing devices described herein, such as the patient care device 102 of FIGS. 1A and 1B, the control unit 104 of FIGS. 1A and 1B, the patient care device 202 of FIG. 2, the patient bio-simulator 310 of FIG. 3, the infusion control system 340 of FIG. 3, the infusion controller 350 of FIG. 3, and the pump simulator 360 of FIG. 3.

In some implementations, one or more of the blocks may be implemented based on one or more machine-learning algorithms. In some implementations, one or more of the blocks may be implemented apart from other blocks, and by one or more different processors or devices. Further, for explanatory purposes, the blocks of the process 500 are described as occurring in serial, or linearly. However, multiple blocks of the process 500 may occur in parallel. Additionally, the blocks of the process 500 need not be performed in the order shown and one or more of the blocks of the process 500 need not be performed whatsoever.

In the depicted example, a simulator (e.g., patient bio-simulator 310, FIG. 3) generates first simulated biophysical data (502). The simulator inputs the simulated data into an infusion control system (e.g., 340, FIG. 3) (504). The infusion control system determines a first infusion profile in response to the first simulated biophysical data (506) and outputs the first infusion profile to an infusion pump simulator (e.g., 360). The infusion pump simulator simulates a first administration of medication according to the first infusion profile (508) and outputs administration data describing the administration back to the simulator, which simulates a patient response to the simulated first administration of medication (510) based on the administration data. The simulator proceeds to generate second simulated biophysical data by adjusting the first simulated biophysical data according to the simulated patient response (512), and the simulator feeds the adjusted simulated biophysiological data back into the infusion control system (back to 504).

The infusion control system proceeds to determine a second infusion profile in response to the second simulated biophysical data; the infusion pump simulator simulates a second administration of medication according to the second infusion profile; and the simulator simulates an updated patient response to the simulated second administration of medication, and generates third simulated biophysical data by adjusting the second simulated biophysical data according to the updated patient response. This process may repeat as necessary (e.g., until simulated biophysical data satisfy a stopping condition of an experiment or reach a predetermined vital sign threshold).

In some implementations, the patient bio-simulator generates the first simulated biophysical data by using one or more algorithms that model patient vital signs. In some implementations, the one or more algorithms use machine learning with existing clinical files to model patient vital signs in response to one or more medications, operations, or scenarios based on multiple patient clinical databases and a cohort of patient models.

In some implementations, the first simulated biophysical data includes a blood pressure level, a blood glucose level, a breathing rate, or an oxygen saturation rate. In some implementations, the second simulated biophysical data includes an adjusted blood pressure level, an adjusted blood glucose level, an adjusted breathing rate, or an adjusted oxygen saturation rate.

In some implementations, the first infusion profile specifies an infusion rate and an infusion amount for a particular medication. In some implementations, the infusion pump simulator simulates the first administration of medication by simulating output of the particular medication in accordance with the infusion rate and the infusion amount.

In some implementations, the first infusion profile specifies an infusion rate for a particular medication, and the infusion pump simulator simulates the first administration of medication according to an accelerated simulation rate that is higher than the infusion rate. In some implementations, the patient bio-simulator simulates the patient response according to the accelerated simulation rate.

The infusion pump testing system 300 and method 500 allow generation of data without complicated patient simulation equipment. The simulator allows testing of the infusion control system without the need for having a patient connected to vital sign monitoring systems, or complicated simulation equipment. Since the data is generated from the simulator, physical equipment is not required to produce the biophysical effects on the patient physiological sensors used to monitor patients. In addition, the inputs themselves are more realistic since they are not simulated from physical machines designed to approximate a living patient.

The infusion pump testing system 300 and method 500 allow time acceleration of the testing system for development and training (also referred to as time compression). The simulator allows accelerating the time signals and system response to allow faster evaluation of system performance without the need to spend hours testing the system behavior. With the ability to accelerate the signal and response times, system development can be reduced. In one example, a medical administration procedure that would take hours in a clinical setting (e.g., a 4-hour surgery) can be simulated in minutes.

The infusion pump testing system 300 and method 500 may be used for training and evaluation. The simulator can be used as a tool to provide training or evaluation of the infusion control system to clinicians without the need to spend hours testing the system behavior. This allows testing without needing to be in a clinical environment with the associated patient risks involved. Combining with time acceleration allows for faster learning to use the infusion pump system during training, and reduces valuable time for clinicians to evaluate the system.

The infusion pump testing system 300 and method 500 allow clinicians and researchers to investigate and model other potential benefits of the infusion control system prior to clinical studies. Simulating patient responses to the infusion control system without using an actual patient reduces development time to allow confirmation of infusion control system performance prior to costly and time-consuming clinical studies. The simulator can also be used to investigate and model other potential benefits of the infusion control system prior to clinical studies. Multiple iterations of workflows can be evaluated and optimized prior to clinical tests. In addition, the infusion pump testing system 300 and method 500 allow for early in-silico testing (performed on computer or via computer simulation) of infusion pump systems.

The infusion pump testing system 300 and method 500 support hazard analysis. The simulator allows the infusion control system to be used to perform hazard analysis prior to human use. This prevents performing hazardous testing on animal or patient subjects. For example, testing the hazard of an IV line disconnecting on the infusion pump could cause an adverse effect to the subject, and performing the test multiple times only increases the risk. As another example, vasopressors may be tested without the hazards involved in blood vessels becoming too narrow in people with low blood pressure. Another example test may involve the simulated disconnecting of one IV line in order to observe the effect the other IV line has on patient consciousness. Another example may involve introducing errors into the training data the simulator receives, thereby adjusting the nominal input stream to observe a corresponding simulated patient response.

Figure 6:
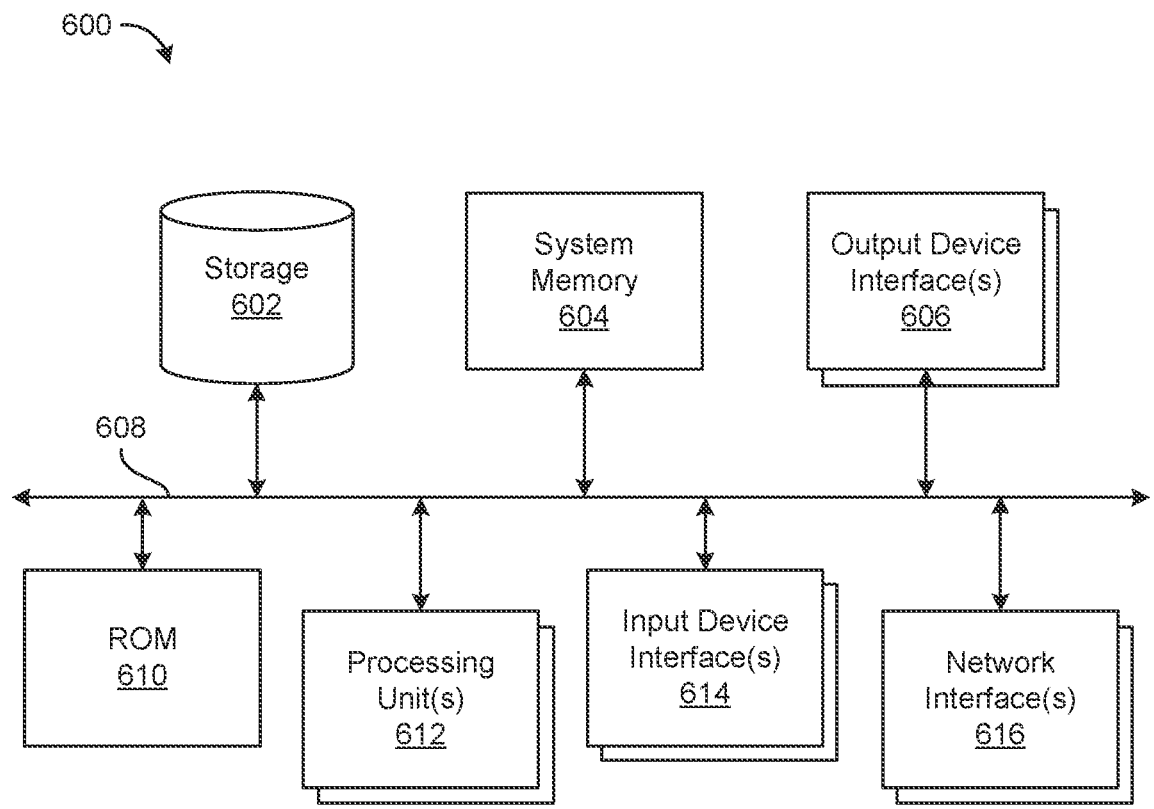
FIG. 6 is a conceptual diagram illustrating an example electronic system for operating an infusion control test system, according to various aspects of the subject technology.

FIG. 6 is a conceptual diagram illustrating an example electronic system 600 for operating an infusion control test system, according to various aspects of the subject technology. The electronic system 600 may be implemented by a computing device for execution of software associated with portions or steps of process 500 of FIG. 5, or components and methods provided by FIGS. 1-4. In this regard, the electronic system 600 may include the patient care device 102 of FIGS. 1A and 1B, the patient care device 202 of FIG. 2, the patient bio-simulator 310 of FIG. 3, the infusion control system 340 of FIG. 3, the infusion controller 350 of FIG. 3, or the pump simulator 360 of FIG. 3.

The electronic system 600 may also include a specifically-configured personal computer or a mobile device for infusion, such as a smartphone, tablet computer, laptop, PDA, an augmented reality device, a wearable such as a watch or band or glasses, or combination thereof, or other touch screen or television with one or more processors embedded therein or coupled thereto, or any other sort of computer-related electronic device having network connectivity.

Additionally, the electronic system 600 may include various types of computer-readable media and interfaces for various other types of computer-readable media. In the depicted example, the electronic system 600 includes a bus 608, a processing unit(s) 612, a system memory 604, a read-only memory (ROM) 610, a permanent storage device 602, an input device interface(s) 614, an output device interface(s) 606, and a network interface(s) 616. In some implementations, electronic system 600 may include or be integrated with other computing devices or circuitry for operation of the various components and methods previously described.

Bus 608 collectively represents system, peripheral, and chipset buses that communicatively connect the numerous internal devices of electronic system 600. For instance, bus 608 communicatively connects processing unit(s) 612 with ROM 610, the system memory 604, and permanent storage device 602. From these various memory units, processing unit(s) 612 retrieves instructions to execute and data to process in order to execute the processes of the subject disclosure. Processing unit(s) 612 can be a single processor or a multi-core processor in different implementations.

ROM 610 stores static data and instructions that are needed by processing unit(s) 612 and other modules of the electronic system. Permanent storage device 602, on the other hand, is a read-and-write memory device. This device is a non-volatile memory unit that stores instructions and data even when electronic system 600 is powered off. Some implementations of the subject disclosure use a mass-storage device (such as a magnetic or optical disk and its corresponding disk drive) as permanent storage device 602. Other implementations use a removable storage device (such as a floppy disk, flash drive, and its corresponding disk drive) as permanent storage device 602.

Like permanent storage device 602, system memory 604 is a read-and-write memory device. However, unlike storage device 602, system memory 604 is a volatile read-and-write memory, such as random-access memory (RAM). System memory 604 stores some of the instructions and data that the processor needs at runtime. In some implementations, the processes of the subject disclosure are stored in system memory 604, permanent storage device 602, and/or ROM 610. From these various memory units, processing unit(s) 612 retrieves instructions to execute and data to process, in order to execute the processes of some implementations.

Bus 608 also connects to input device interface(s) 614 and output device interface(s) 606. Input device interface(s) 614 enables the user to communicate information and select commands to the electronic system. Input devices used with input device interface(s) 614 include, for example, alphanumeric keyboards and pointing devices (also called "cursor control devices"). Output device interface(s) 606 enables, for example, the display of images generated by electronic system 600. Output devices used with output device interface(s) 606 include, for example, printers and display devices, such as cathode ray tubes (CRT) or liquid crystal displays (LCD). Some implementations include devices (e.g., touchscreens) that function as both input and output devices.

Furthermore, bus 608 also couples electronic system 600 to a network (not shown) through network interface(s) 616. Network interface(s) 616 may include, for example, a wireless access point (e.g., Bluetooth or Wi-Fi) or radio circuitry for connecting to a wireless access point. Network interface(s) 616 may also include hardware (e.g., ethernet hardware) for connecting the computer to a part of a network of computers such as a local area network (LAN), a wide area network (WAN), wireless LAN, an intranet, or a network of networks, such as the Internet. Components of electronic system 600 can be used in conjunction with the subject disclosure when specifically configured with one of more of the features described.

The functions described above can be implemented in computer software, firmware, or hardware. The techniques can be implemented using one or more computer program products. Programmable processors and computers can be included in or packaged as mobile devices. The processes and logic flows can be performed by one or more programmable processors and by programmable logic circuitry. General and special purpose computing devices and storage devices can be interconnected through communication networks.

Some implementations include electronic components, such as microprocessors, storage and memory that store computer program instructions in a machine-readable or computer-readable medium (also referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field-programmable gate arrays (FPGAs). In some implementations, such integrated circuits execute instructions that are stored on the circuit itself.

As used in this specification and any claims of this application, the terms "computer," "server," "processor," and "memory" all refer to electronic or other technological devices specifically configured with one or more of the features described above. These terms exclude people or groups of people. For the purposes of the specification, the terms display or displaying means displaying on an electronic device. As used in this specification and any claims of this application, the terms "computer-readable medium" and "computer-readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well. For example, feedback provided to the user can be any form of sensory feedback (e.g., visual feedback, auditory feedback, tactile feedback), and input from the user can be received in forms such as acoustic, speech, gesture, or tactile input. In addition, a computer can interact with a user by sending documents to and receiving documents from a device that is used by the user (e.g., by sending web pages to a web browser on a user's client device in response to requests received from the web browser).

Implementations of the subject matter described in this specification can be implemented in a specifically configured computing system that includes a back end component (e.g., a data server), or that includes a specifically configured middleware component (e.g., an application server), or that includes a specifically configured front end component (e.g., a client computer having a graphical user interface or a Web browser through which a user can interact with an implementation of the subject matter described in this specification), or any combination of one or more such back end, middleware, or front end components. The components of the system can be interconnected by one or more forms or mediums of digital data communication, such as a communication network. Examples of communication networks include a LAN and a WAN, an inter-network (e.g., the Internet), and peer-to-peer networks (e.g., ad hoc peer-to-peer networks).

The computing system can include specifically configured clients and servers. A client and server are generally remote from each other and may interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Those of skill in the art will appreciate that the various illustrative blocks, modules, elements, components, methods, and algorithms described herein may be implemented as electronic hardware, computer software, or a combination thereof. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. The described functionality may be implemented in varying ways for each particular application. Various components and blocks may be arranged differently (e.g., arranged in a different order, or partitioned in a different way) all without departing from the scope of the subject technology.

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order and are not meant to be limited to the specific order or hierarchy presented.

Illustration of Subject Technology as Clauses:

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1: An infusion control test system comprising: a patient bio-simulator configured to generate first simulated biophysical data; an infusion control system configured to determine a first infusion profile in response to the first simulated biophysical data; and an infusion pump simulator configured to simulate a first administration of medication according to the first infusion profile; wherein the patient bio-simulator is further configured to: simulate a patient response to the simulated first administration of medication; and generate second simulated biophysical data by adjusting the first simulated biophysical data according to the patient response.

Clause 2: The infusion control test system of clause 1, wherein: the infusion control system is further configured to determine a second infusion profile in response to the second simulated biophysical data; the infusion pump simulator is further configured to simulate a second administration of medication according to the second infusion profile; and the patient bio-simulator is further configured to: simulate an updated patient response to the simulated second administration of medication; and generate third simulated biophysical data by adjusting the second simulated biophysical data according to the updated patient response.

Clause 3: The infusion control test system of clause 1 or clause 2, wherein the patient bio-simulator is configured to generate the first simulated biophysical data by using one or more algorithms that model patient vital signs.

Clause 4: The infusion control test system of clause 3, wherein the one or more algorithms use machine learning with existing clinical files to model patient vital signs in response to one or more medications, operations, or scenarios based on multiple patient clinical databases and a cohort of patient models.

Clause 5: The infusion control test system of any one of clauses 1-4, wherein the first simulated biophysical data includes a blood pressure level, a blood glucose level, a breathing rate, or an oxygen saturation rate.

Clause 6: The infusion control test system of clause 5, wherein the second simulated biophysical data includes an adjusted blood pressure level, an adjusted blood glucose level, an adjusted breathing rate, or an adjusted oxygen saturation rate.

Clause 7: The infusion control test system of any one of clauses 1-6, wherein the first infusion profile specifies an infusion rate and an infusion amount for a particular medication.

Clause 8: The infusion control test system of clause 7, wherein the infusion pump simulator is configured to simulate the first administration of medication by simulating output of the particular medication in accordance with the infusion rate and the infusion amount.

Clause 9: The infusion control test system of any one of clauses 1-8, wherein the first infusion profile specifies an infusion rate for a particular medication, and the infusion pump simulator is configured to simulate the first administration of medication according to an accelerated simulation rate that is higher than the infusion rate.

Clause 10: The infusion control test system of clause 9, wherein the patient bio-simulator is configured to simulate the patient response according to the accelerated simulation rate.

Clause 11: A computer-implemented method for operating an infusion control test system, the method comprising: causing a patient bio-simulator to generate first simulated biophysical data; causing an infusion control system to determine a first infusion profile in response to the first simulated biophysical data; causing an infusion pump simulator to simulate a first administration of medication according to the first infusion profile; and causing the patient bio-simulator to: simulate a patient response to the simulated first administration of medication; and generate second simulated biophysical data by adjusting the first simulated biophysical data according to the patient response.

Clause 12: The method of clause 11, wherein: the infusion control system is further configured to determine a second infusion profile in response to the second simulated biophysical data; the infusion pump simulator is further configured to simulate a second administration of medication according to the second infusion profile; and the patient bio-simulator is further configured to: simulate an updated patient response to the simulated second administration of medication; and generate third simulated biophysical data by adjusting the second simulated biophysical data according to the updated patient response.

Clause 13: The method of clause 11 or clause 12, wherein the patient bio-simulator is configured to generate the first simulated biophysical data by using one or more algorithms that model patient vital signs.

Clause 14: The method of clause 13, wherein the one or more algorithms use machine learning with existing clinical files to model patient vital signs in response to one or more medications, operations, or scenarios based on multiple patient clinical databases and a cohort of patient models.

Clause 15: The method of any one of clauses 11-14, wherein the first simulated biophysical data includes a blood pressure level, a blood glucose level, a breathing rate, or an oxygen saturation rate.

Clause 16: The method of clause 15, wherein the second simulated biophysical data includes an adjusted blood pressure level, an adjusted blood glucose level, an adjusted breathing rate, or an adjusted oxygen saturation rate.

Clause 17: The method of any one of clauses 11-16, wherein the first infusion profile specifies an infusion rate and an infusion amount for a particular medication.

Clause 18: The method of clause 17, wherein the infusion pump simulator is configured to simulate the first administration of medication by simulating output of the particular medication in accordance with the infusion rate and the infusion amount.

Clause 19: The method of any one of clauses 11-18, wherein the first infusion profile specifies an infusion rate for a particular medication, and the infusion pump simulator is configured to simulate the first administration of medication according to an accelerated simulation rate that is higher than the infusion rate.

Clause 20: The method of clause 19, wherein the patient bio-simulator is configured to simulate the patient response according to the accelerated simulation rate.

Further Consideration

It is understood that the specific order or hierarchy of steps in the processes disclosed herein is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention described herein.

The predicate words "configured to," "operable to," and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

The term automatic, as used herein, may include performance by a computer or machine without user intervention; for example, by instructions responsive to a predicate action by the computer or machine or other initiation mechanism. The word "example" is used herein to mean "serving as an example or illustration." Any aspect or design described herein as "example" is not necessarily to be construed as preferred or advantageous over other aspects or designs.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "implementation" does not imply that such implementation is essential to the subject technology or that such implementation applies to all configurations of the subject technology. A disclosure relating to an implementation may apply to all implementations, or one or more implementations. An implementation may provide one or more examples. A phrase such as an "implementations" may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

As used herein a "user interface" (also referred to as an interactive user interface, a graphical user interface or a UI) may refer to a network based interface including data fields and/or other control elements for receiving input signals or providing electronic information and/or for providing information to the user in response to any received input signals. Control elements may include dials, buttons, icons, selectable areas, or other perceivable indicia presented via the UI that, when interacted with (e.g., clicked, touched, selected, etc.), initiates an exchange of data for the device presenting the UI. A UI may be implemented in whole or in part using technologies such as hyper-text mark-up language (HTML), FLASH™, JAVA™, NET™, C, C++, web services, or rich site summary (RSS). In some implementations, a UI may be included in a stand-alone client (for example, thick client, fat client) configured to communicate (e.g., send or receive data) in accordance with one or more of the aspects described. The communication may be to or from a medical device or server in communication therewith.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "message" encompasses a wide variety of formats for communicating (e.g., transmitting or receiving) information. A message may include a machine readable aggregation of information such as an XML document, fixed field message, comma separated message, JSON, a custom protocol, or the like. A message may, in some implementations, include a signal utilized to transmit one or more representations of the information. While recited in the singular, it will be understood that a message may be composed, transmitted, stored, received, etc. in multiple parts.

As used herein, the term "selectively" or "selective" may encompass a wide variety of actions. For example, a "selective" process may include determining one option from multiple options. A "selective" process may include one or more of: dynamically determined inputs, preconfigured inputs, or user-initiated inputs for making the determination. In some implementations, an n-input switch may be included to provide selective functionality where n is the number of inputs used to make the selection.

As used herein, the terms "correspond" or "corresponding" encompasses a structural, functional, quantitative and/or qualitative correlation or relationship between two or more objects, data sets, information and/or the like, preferably where the correspondence or relationship may be used to translate one or more of the two or more objects, data sets, information and/or the like so to appear to be the same or equal. Correspondence may be assessed using one or more of a threshold, a value range, fuzzy logic, pattern matching, a machine-learning assessment model, or combinations thereof.

In any implementation, data generated or detected can be forwarded to a "remote" device or location, where "remote," means a location or device other than the location or device at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like.

What is claimed is:

1. An infusion control test system comprising:
    a patient bio-simulator configured to generate first simulated biophysical data based on a plurality of different algorithms provided by each of a plurality of different patient simulation models that model patient responses, wherein each of the algorithms results from machine learning used with existing clinical files;
    an infusion control system configured to determine a first infusion profile in response to the first simulated biophysical data; and
    an infusion pump simulator configured to simulate a first administration of medication according to the first infusion profile;
    wherein the patient bio-simulator is further configured to:
        simulate a patient response to the simulated first administration of medication based on the plurality of different algorithms provided by each of a plurality of different patient simulation models; and
        generate second simulated biophysical data by adjusting the first simulated biophysical data according to the patient response.

2. The infusion control test system of claim 1, wherein:
    the infusion control system is further configured to determine a second infusion profile in response to the second simulated biophysical data;
    the infusion pump simulator is further configured to simulate a second administration of medication according to the second infusion profile; and
    the patient bio-simulator is further configured to:
        simulate an updated patient response to the simulated second administration of medication based on the plurality of different algorithms provided by each of a plurality of different patient simulation models; and
        generate third simulated biophysical data by adjusting the second simulated biophysical data according to the updated patient response.

3. The infusion control test system of claim 1, wherein the patient bio-simulator is configured to generate the first simulated biophysical data by using one or more algorithms that model patient vital signs.

4. The infusion control test system of claim 3, wherein the one or more algorithms use machine learning with existing clinical files to model patient vital signs in response to one or more medications, operations, or scenarios based on multiple patient clinical databases and a cohort of patient models.

5. The infusion control test system of claim 1, wherein the first simulated biophysical data includes a blood pressure level, a blood glucose level, a breathing rate, or an oxygen saturation rate.

6. The infusion control test system of claim 5, wherein the second simulated biophysical data includes an adjusted blood pressure level, an adjusted blood glucose level, an adjusted breathing rate, or an adjusted oxygen saturation rate.

7. The infusion control test system of claim 1, wherein the first infusion profile specifies an infusion rate and an infusion amount for a particular medication.

8. The infusion control test system of claim 7, wherein the infusion pump simulator is configured to simulate the first administration of medication by simulating output of the particular medication in accordance with the infusion rate and the infusion amount.

9. The infusion control test system of claim 1, wherein the first infusion profile specifies an infusion rate for a particular medication, and the infusion pump simulator is configured to simulate the first administration of medication according to an accelerated simulation rate that is higher than the infusion rate.

10. The infusion control test system of claim 9, wherein the patient bio-simulator is configured to simulate the patient response according to the accelerated simulation rate.

11. A computer-implemented method for operating an infusion control test system, the method comprising:
    causing a patient bio-simulator to generate first simulated biophysical data based on a plurality of different algorithms provided by each of a plurality of different patient simulation models that model patient responses, wherein each of the algorithms results from machine learning used with existing clinical files;
    causing an infusion control system to determine a first infusion profile in response to the first simulated biophysical data;
    causing an infusion pump simulator to simulate a first administration of medication according to the first infusion profile; and
    causing the patient bio-simulator to:
        simulate a patient response to the simulated first administration of medication based on the plurality of different algorithms provided by each of a plurality of different patient simulation models; and
        generate second simulated biophysical data by adjusting the first simulated biophysical data according to the patient response.

12. The method of claim 11, wherein:
    the infusion control system is further configured to determine a second infusion profile in response to the second simulated biophysical data;
    the infusion pump simulator is further configured to simulate a second administration of medication according to the second infusion profile; and the patient bio-simulator is further configured to:
   simulate an updated patient response to the simulated second administration of medication based on the plurality of different algorithms provided by each of a plurality of different patient simulation models; and
   generate third simulated biophysical data by adjusting the second simulated biophysical data according to the updated patient response.

13. The method of claim 11, wherein the patient bio-simulator is configured to generate the first simulated biophysical data by using one or more algorithms that model patient vital signs.

14. The method of claim 13, wherein the one or more algorithms use machine learning with existing clinical files to model patient vital signs in response to one or more medications, operations, or scenarios based on multiple patient clinical databases and a cohort of patient models.

15. The method of claim 11, wherein the first simulated biophysical data includes a blood pressure level, a blood glucose level, a breathing rate, or an oxygen saturation rate.

16. The method of claim 15, wherein the second simulated biophysical data includes an adjusted blood pressure level, an adjusted blood glucose level, an adjusted breathing rate, or an adjusted oxygen saturation rate.

17. The method of claim 11, wherein the first infusion profile specifies an infusion rate and an infusion amount for a particular medication.

18. The method of claim 17, wherein the infusion pump simulator is configured to simulate the first administration of medication by simulating output of the particular medication in accordance with the infusion rate and the infusion amount.

19. The method of claim 11, wherein the first infusion profile specifies an infusion rate for a particular medication, and the infusion pump simulator is configured to simulate the first administration of medication according to an accelerated simulation rate that is higher than the infusion rate.

20. The method of claim 19, wherein the patient bio-simulator is configured to simulate the patient response according to the accelerated simulation rate.

* * * * *